(12) United States Patent
Lux et al.

(10) Patent No.: US 10,524,899 B2
(45) Date of Patent: Jan. 7, 2020

(54) MULTIFOCAL LENS AND METHOD FOR PRODUCING SAME

(71) Applicant: Rayner Intraocular Lenses Limited, West Sussex (GB)

(72) Inventors: Kirsten Lux, Mödling (AT); Nicole Plank, Forchtenstein (AT); Wolfgang Brezna, Wiener Neustadt (AT); Nikolaus Dragostinoff, Vienna (AT)

(73) Assignee: Rayner Intraocular Limited, West Sussex (GB)

( * ) Notice: Subject to any disclaimer, the term of this patent is extended or adjusted under 35 U.S.C. 154(b) by 0 days.

(21) Appl. No.: 15/765,385

(22) PCT Filed: Sep. 29, 2016

(86) PCT No.: PCT/EP2016/073349
§ 371 (c)(1),
(2) Date: Apr. 2, 2018

(87) PCT Pub. No.: WO2017/055503
PCT Pub. Date: Apr. 6, 2017

(65) Prior Publication Data
US 2018/0303601 A1 Oct. 25, 2018

(30) Foreign Application Priority Data
Oct. 2, 2015 (EP) .................................. 15188049

(51) Int. Cl.
*A61F 2/16* (2006.01)
*G02C 7/04* (2006.01)

(52) U.S. Cl.
CPC ............ *A61F 2/1618* (2013.01); *A61F 2/164* (2015.04); *A61F 2/1656* (2013.01); *G02C 7/044* (2013.01); *G02C 2202/20* (2013.01)

(58) Field of Classification Search
CPC ...... A61F 2/1618; A61F 2/1637; A61F 2/164; A61F 2/1654; A61F 2/1656;
(Continued)

(56) References Cited

U.S. PATENT DOCUMENTS 4,210,391 A * 7/1980 Cohen .................. G02B 5/1876
351/159.39
4,340,283 A * 7/1982 Cohen .................. G02B 5/1876
351/159.41

(Continued)

FOREIGN PATENT DOCUMENTS

CA 2700890 A1 7/2009
CA 2787986 A1 8/2011
(Continued)

*Primary Examiner* — Paul B Prebilic
(74) *Attorney, Agent, or Firm* — Hodgson Russ LLP (57) ABSTRACT

The invention relates to a multifocal lens (1), in particular an intraocular lens or contact lens, having a refractive focus ($F_r$) and a first and a second diffractive structure (6, 7) that at least partially overlap, said two diffractive structures (6, 7) being different. A first order focus ($F_{1;1}$) of the first diffractive structure (6) coincides with a first order focus ($F_{2;1}$) of the second diffractive structure (7). The invention further relates to a method for producing such a multifocal lens (1).

20 Claims, 5 Drawing Sheets

(58) Field of Classification Search
CPC ..... A61F 2250/0091; A61F 2250/0053; G02C 7/044; G02C 2202/20
See application file for complete search history.

(56) References Cited

U.S. PATENT DOCUMENTS

| | | | | |
|---|---|---|---|---|
| 5,017,000 | A * | 5/1991 | Cohen | A61F 2/1618 351/159.41 |
| 5,117,306 | A * | 5/1992 | Cohen | G02B 5/1876 351/159.11 |
| 5,760,871 | A | 6/1998 | Kosoburd et al. | |
| 6,536,899 | B1 * | 3/2003 | Fiala | A61F 2/1654 351/159.44 |
| 6,873,463 | B2 * | 3/2005 | Nakai | G02B 5/1814 359/565 |
| 9,658,471 | B2 * | 5/2017 | Ando | G02C 7/044 |
| 2006/0116764 | A1 | 6/2006 | Simpson | |
| 2006/0176572 | A1 * | 8/2006 | Fiala | A61F 2/16 359/643 |
| 2009/0195748 | A1 * | 8/2009 | Bandhauer | A61F 2/1618 351/159.47 |
| 2009/0268155 | A1 | 10/2009 | Weeber | |
| 2010/0066973 | A1 | 3/2010 | Portney | |
| 2011/0234974 | A1 | 9/2011 | Lawu | |
| 2011/0267693 | A1 | 11/2011 | Kobayashi et al. | |
| 2011/0270390 | A1 * | 11/2011 | Kobayashi | A61F 2/1618 623/6.38 |
| 2012/0140166 | A1 * | 6/2012 | Zhao | A61F 2/1618 351/159.15 |
| 2014/0347624 | A1 | 11/2014 | Ando et al. | |
| 2017/0227789 | A1 * | 8/2017 | Ando | A61L 27/00 |

FOREIGN PATENT DOCUMENTS

| | | |
|---|---|---|
| CN | 101416097 A | 4/2009 |
| DE | 202009018881 U1 | 2/2014 |
| EP | 2503962 B1 | 7/2013 |
| JP | 2005292860 A | 10/2005 |
| JP | 2008518281 A | 5/2008 |
| JP | 2013517822 A | 5/2013 |
| RU | 2538935 C2 | 1/2015 |
| WO | 2010079528 A1 | 7/2010 |

* cited by examiner

MULTIFOCAL LENS AND METHOD FOR PRODUCING SAME

CROSS-REFERENCE TO RELATED APPLICATIONS

This application is a National Phase of PCT/EP2016/073349, filed Sep. 29, 2016, which claims priority to European Patent Application No. 15188049.9, filed Oct. 2, 2015, the disclosure of which is incorporated herein by reference.

FIELD OF THE DISCLOSURE

The present invention relates to a multifocal intraocular or contact lens, with a refractive focal point and a first and a second diffractive structure, which at least partially overlap. In a further aspect, the invention relates to a method for producing such a multifocal lens.

BACKGROUND OF THE DISCLOSURE

Multifocal intraocular or contact lenses, i.e. lenses with a plurality of focal points, which may for example be used for near and distance vision (bifocal) or near, intermediate and distance vision (trifocal), have been known for several decades and use a very wide range of diffractive structures on a refractive basic lens, in order to provide one or more diffractive focal points in addition to the refractive focal point.

According to documents DE 20 2009 018 881 U1 and EP 2 503 962 B1, two diffractive structures each of kinoform profile are overlapped. One of the two diffractive structures here has a first order focal point, which coincides with the second order focal point. The applicant has recognised that calculating such structures is extremely complicated. In addition, incorporating such structures into the lens leads to a plurality of profile peaks which are difficult to manufacture, resulting in turn in suboptimal distribution or light yield of the light intensities in the focal points produced. A multifocal intraocular or contact lens according to the preamble of claim 1 is known from document US-A-2011/0267693. The object of the invention is to provide an improved lens which overcomes the disadvantages of the prior art.

SUMMARY OF THE DISCLOSURE

According to a first aspect of the invention, the objective is achieved with a lens of the above-mentioned type, in which the two diffractive structures are different, and wherein a first order focal point of the first diffractive structure coincides with a first order focal point of the second diffractive structure.

By overlapping the two diffractive structures with coinciding first order focal points, calculation of the overlapping diffractive structure may be considerably simplified, since the structures to be overlapped each have a profile with the same periodic lengths. Adjustments to the structures to determine an optimum intensity distribution during calculation may thus be made particularly simply.

The two diffractive structures preferably have different intensity distributions, whereby an individual mixture of intensity ratios is possible.

A particularly advantageous embodiment of the invention is distinguished in that the first diffractive structure has an intensity distribution that is asymmetric around the refractive focal point and the second diffractive structure has an intensity distribution that is substantially symmetric around the refractive focal point.

By overlapping these two diffractive structures, a lens is provided whose focal points usable for near, intermediate and distance vision have a higher intensity component than is known in the prior art. For more precise consideration of the problem, "positive" order diffractive focal points will hereinafter be defined as those which are located between the lens and its refractive focal point, and "negative" order diffractive focal points as those which are located on the side of the refractive focal point remote from the lens.

If the refractive focal point is used for distance vision, for example, the first positive order focal point of the diffractive structures corresponds to a distance for intermediate vision and the second positive order focal point of the diffractive structures to a distance for near vision. The respective negative focal points of the diffractive structures will in this case form an image only behind the lens user's retina, for which reason they are not useful to the user and contribute to an impairment of image quality.

By the overlapping according to the invention of a diffractive structure with symmetrical intensity distribution with a diffractive structure with asymmetric intensity distribution, in contrast, the (originally) negative orders are imaged onto the positive orders used or onto the zeroth (refractive) order, resulting in a more intensely coloured, higher contrast image compared to the prior art, since the useful focal points comprise higher intensity components.

The same advantages are obtained if, for example in an alternative embodiment, the refractive focal point is used for near vision, and the first negative order focal point of the overlapping structure corresponds to a distance for intermediate vision and the second negative order focal point of the overlapping structure corresponds to a distance for distance vision. In this embodiment, the positive orders of the diffractive structures are of little use, since they are located in front of the near vision focal point, and the third negative order orders are of no use at all, since they are only focused behind the retina. According to the invention, intensity components of the positive orders are imaged onto the zeroth (refractive) negative first and negative second order, again resulting in a higher light yield in the useful focal points and thus a more intensely coloured, higher contrast image compared to the prior art.

Preferably, the profiles of the two diffractive structures have the same period length, wherein the profile of the first diffractive structure rises monotonically within the period and the profile of the second diffractive structure has a minimum in the first half of the period and a maximum in the second half of the period. This ensures that the resultant profile of the lens has a small number of profile peaks. Such peaks are difficult to manufacture and lead, if manufactured imprecisely, to errors in the image area, resulting in a fuzzy or blurred image for the observer. For example, the first diffractive structure, i.e. the structure with asymmetric intensity distribution, has a profile with saw-tooth, echelette or kinoform shape and the second diffractive structure, i.e. the structure with the substantially symmetric intensity distribution, has a profile with rectangular, trapezoidal or sinusoidal shape. In this way, profile curves may be used whose behaviour is well known and which additionally enable easy manufacture.

According to a preferred feature of the invention, at least one of the profiles may have rounded-off or bevelled flanks.

As a result, manufacturing processes with lower tolerances may be selected, so minimising both manufacturing costs and manufacturing time.

In a further advantageous embodiment of the invention, the two diffractive structures overlap only in a central region of the lens. The lens may for example not have any diffractive structure at all outside the central region. If the pupil dilates, for example in the event of low light incidence, the influence of the non-central region or of the refractive component for distance vision increases, such that in the case of such pupil sizes the intensity distribution merely comprises distance vision. Alternatively, the lens may also comprise just one of the two diffractive structures outside the central region, whereby for example the near and distance vision or the intermediate and distance vision may be at its greatest in the case of wide pupils.

The two diffractive structures are preferably apodised, preferably at different strengths, in the radial direction of the lens. This ensures that, in the case of a small pupil, the intensity distribution is different from in the case of a large pupil. This also results in a continuous transition in the change in intensity distribution when pupils are dilating or contracting. If different strengths of apodisation are selected, the intensity distributions may be adapted as desired to the desired pupil size.

The lens of the invention may in principle be used in any desired optical devices, but it is particularly suitable as a multifocal contact or intraocular lens.

According to a second aspect, the invention also provides a method for producing the lens presented here. In a first embodiment, the method comprises the following steps:
a) providing a lens blank with a refractive focal point;
b) calculating an overlapping structure from a first diffractive structure and a second diffractive structure, wherein the two diffractive structures are different, and wherein a first order focal point of the first diffractive structure coincides with a first order focal point of the second diffractive structure; and
c) incorporating the overlapping structure into the lens blank to produce the multifocal lens.

The step of incorporating the overlapping structure into the lens blank is preferably realised by turning, which enables particularly precise manufacture of the multifocal lens.

In a second embodiment, the method comprises the following steps:
a) providing a moulded blank;
b) calculating an overlapping structure from a first diffractive structure and a second diffractive structure, wherein the two diffractive structures are different, and wherein a first order focal point of the first diffractive structure coincides with a first order focal point of the second diffractive structure;
c) incorporating the overlapping structure as a negative into the moulded blank; and
d) producing the multifocal lens by bringing a lens material into contact with the moulded blank, wherein a refractive focal point is also given to the lens material.

In this embodiment, first of all a moulded blank with the overlapping structure, i.e. a "negative mould", is produced, for example by turning or milling. The lens is then cast, pressed, printed or otherwise shaped by means of the negative mould.

The bringing into contact is preferably realised by casting the lens material onto the moulded blank and hardening the lens material. The lens material may in this case solidify by itself or be hardened for example by means of light or heat treatment.

The two embodiments of the method according to the invention are distinguished by a simple calculation of the overlapping structure, two structures for example being overlapped by simple addition, which requires only slight computing power.

In the two embodiments, it is particularly preferable for the first diffractive structure to have an intensity distribution that is asymmetric around the refractive focal point and for the second diffractive structure to have an intensity distribution that is substantially symmetric around the refractive focal point.

As far as further features and advantages of the method according to the invention for producing the multifocal lens are concerned, reference is made to the above-stated features and advantages of the lens according to the invention.

BRIEF DESCRIPTION OF THE FIGURES

The invention is explained in greater detail below with reference to exemplary embodiments depicted in the appended drawings, in which.

DETAILED DESCRIPTION OF THE DISCLOSURE

Figure 1:
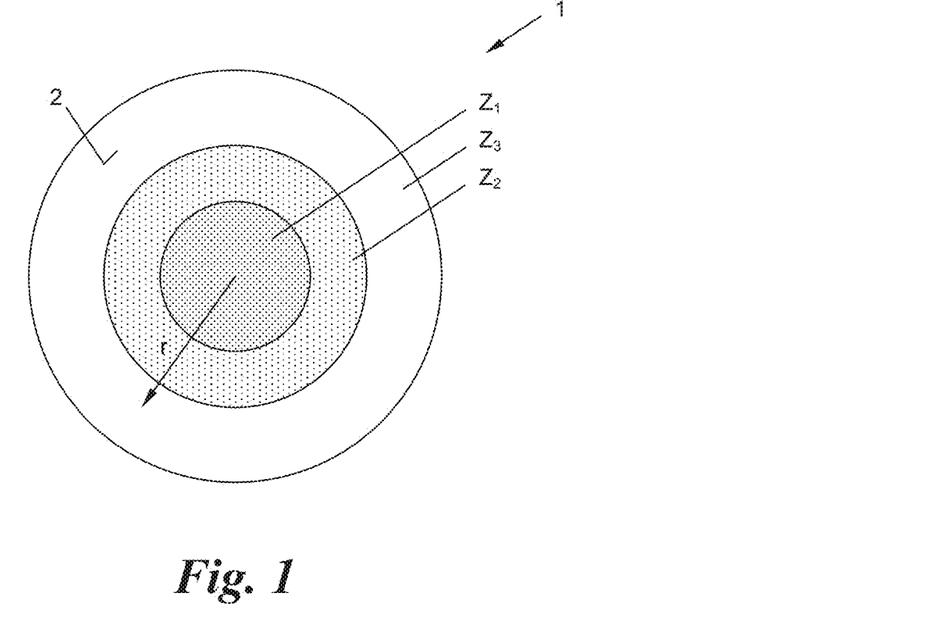
FIG. 1 is a schematic plan view of the lens according to the invention.
Figure 2:
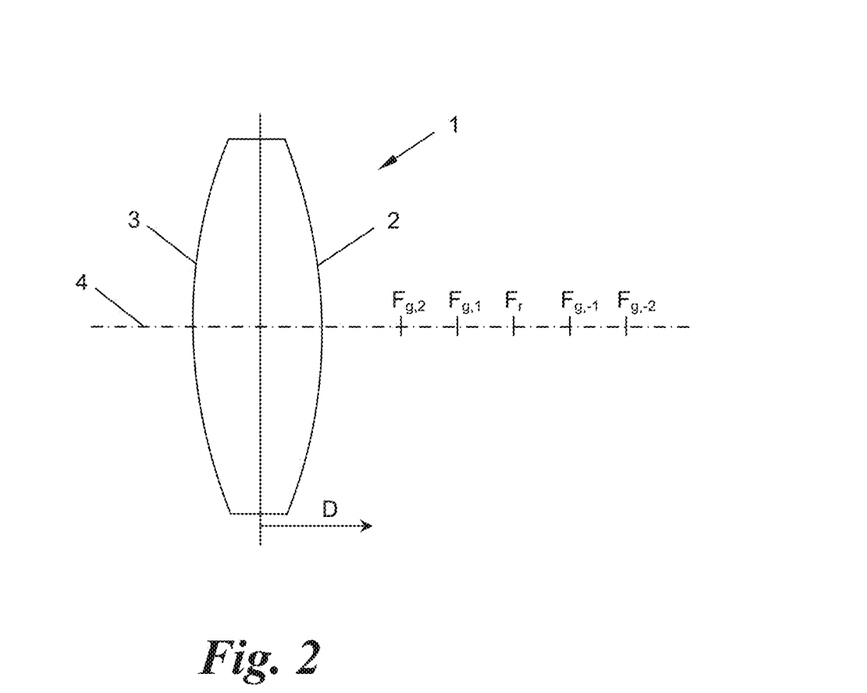
FIG. 2 is a schematic side view of the lens of FIG. 1.

FIGS. 1 and 2 show a lens 1 with a front 2, a back 3 and an optical axis 4. The lens 1 has a central zone $Z_1$ and two annular zones $Z_2$, $Z_3$, which will be explained in greater detail below. The described lens 1 is used as an intraocular lens or contact lens, but may also be used in optical equipment.

Figure 4:
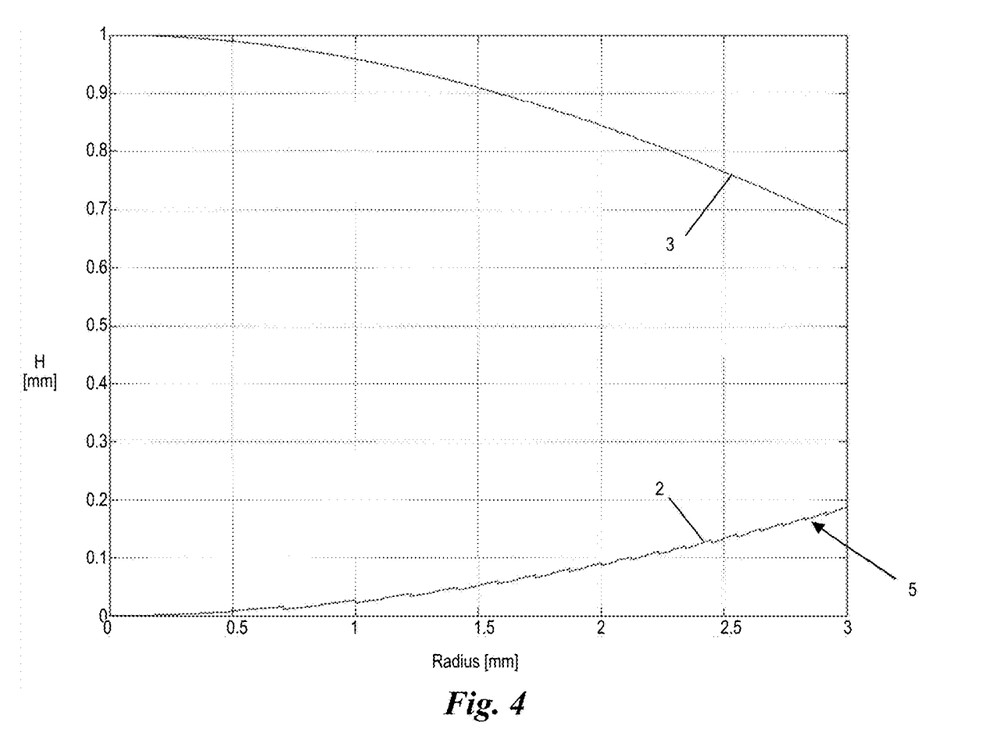
FIG. 4 is an enlarged half section of the lens of FIG. 1 with the overlapping structure of FIG. 3.

The lens 1 has a refractive focal point $F_r$ located on the optical axis 4, which focal point may be used, as described below, for distance or near vision and is also described hereinafter as a zeroth order focal point. A diffractive structure 5 is incorporated into the back or front 2, 3 of the lens 1, see FIG. 4, in order to adapt the lens 1 both to near and to intermediate and distance vision.

The diffractive structure 5 generates a plurality of further focal points $F_{g,i}$, i=−2, −1, 1, 2 etc. located on the optical axis 4 which are distributed substantially symmetrically around the refractive focal point $F_r$, wherein the refractive focal point $F_r$ is provided by the shape of the lens 1, irrespective of the diffractive structure 5 applied. The diffractive focal points $F_{g,1}$, $F_{g,2}$ are described as positive first or second order focal points of the diffractive structure 5 and lie on the optical axis 4 between the lens 1 and the refractive focal point $F_r$. The diffractive focal points $F_{g,-1}$, $F_{g,-2}$ are described as negative first or second order focal points of the diffractive structure 5 and lie on the side of the refractive focal point $F_r$ remote from the lens 1.

Although the (positional) distribution of the focal points $F_{g,i}$ is substantially symmetrical around the refractive focal point $F_r$, the intensity distribution assigned to the respective focal points $F_{g,i}$ is not intended to be symmetrical. For instance, in the case of a trifocal lens in particular three maximum intensities form, namely for distance, intermediate and near vision. This is achieved by forming the diffractive structure 5 as follows from a first and a second diffractive structure 6, 7, these overlapping in at least one of zones $Z_1$, $Z_2$, $Z_3$.

Figure 3:
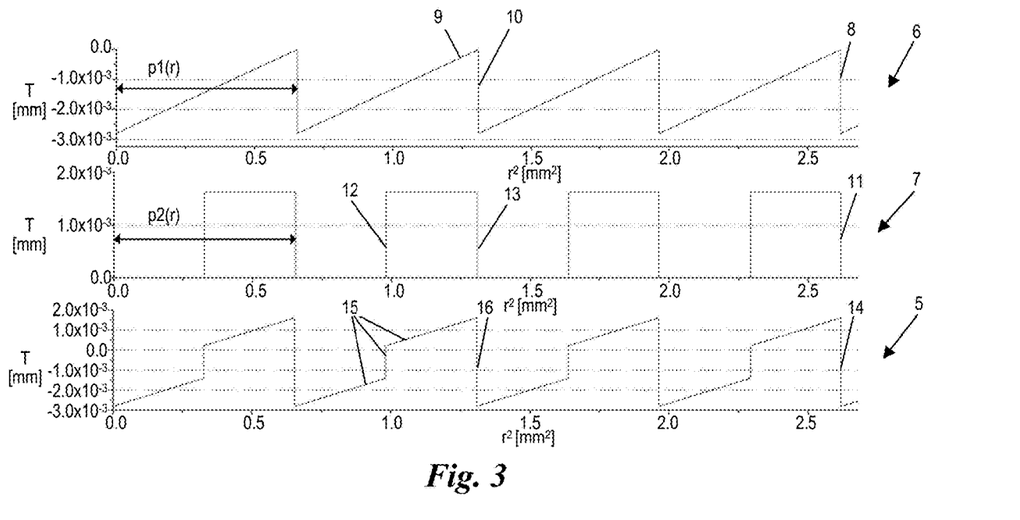
FIG. 3 shows profiles of a first and a second diffractive structure and the profile of an overlapping structure resulting from the overlapping of the first and second structures for the lens of FIG. 1.

The top diagram of FIG. 3 shows the profile 11 of the first diffractive structure 6 (x-axis: radius $r^2$ [mm$^2$]; y-axis: profile depth T [mm]). The first diffractive structure 6 has a grating period $p_1(r)$ which is dependent on the radius r, more specifically on $r^2$. If the structure 6 is plotted over $r^2$ as an x-axis scale, the period $p_1$ occurs in equidistant repetitions over the x-axis.

The first diffractive structure 6 has an asymmetric intensity distribution around the refractive focal point $F_r$ in its diffractive focal points $F_{1,i}$, see FIG. 5 below, and to this end has a profile 8 with asymmetrically rising and falling flanks 9, 10 plotted over the squared radius $r^2$, wherein one of the flanks 9, 10 may be vertical.

FIG. 3 shows the first, saw-tooth-shaped diffractive structure 6, though this may also have an echelette or kinoform shape. The grating period $p_1(r)$ determines the distance between the focal points $F_{1,i}$ generated by the first diffractive structure 6 and the refractive focal point $F_r$.

The middle diagram of FIG. 3 shows the profile of the second diffractive structure 7 (x-axis: radius $r^2$ [mm$^2$]; y-axis: profile depth T [mm]). The second diffractive structure 7 has a grating period $p_2(r)$ which is dependent on the radius r, more specifically on $r^2$. If the structure 7 is plotted over $r^2$ as an x-axis scale, the period $p_2$ occurs in equidistant repetitions over the x-axis.

Figure 5:
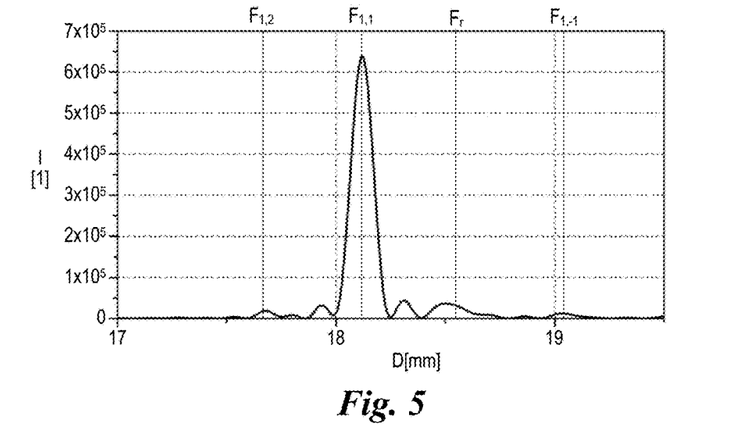
FIG. 5 shows the intensity distribution of a lens equipped with the first diffractive structure of FIG. 3.

The second diffractive structure 7 has an intensity distribution in its diffractive focal points $F_{2,i}$ which is substantially symmetrical about the refractive focal point $F_r$, as explained in still greater detail with reference to FIG. 5. The structure 7 to this end comprises a profile with flanks 12, 13 which rise and fall substantially symmetrically relative to one another, plotted over the squared radius $r^2$, said flanks preferably being vertical. The term "substantially symmetrically" here in each case encompasses slight deviations from symmetry.

FIG. 3 shows the second diffractive structure 7 as a binary structure, i.e. with a rectangular shape. Alternatively, however, it could for example also be trapezoidal or sinusoidal in shape. The grating period $p_2(r)$ determines the distance between the focal points $F_{2,i}$ generated by the second diffractive structure 7 and the refractive focal point $F_r$.

FIG. 5 shows the intensity distribution of a lens, onto which just a first diffractive structure 6 according to the top diagram of FIG. 3 has been plotted (x-axis: distance D from the lens [mm]; y-axis: relative intensity I [1]). As shown, the intensity distribution of the diffractive focal points $F_{1,i}$ is asymmetric around the refractive focal point.

Figure 6:
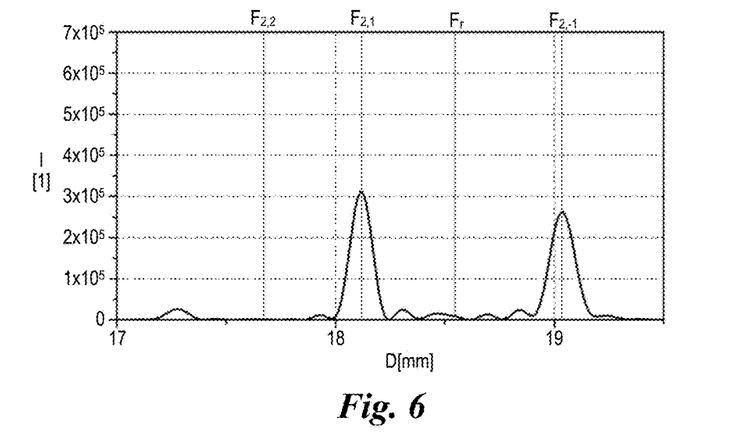
FIG. 6 shows the intensity distribution of a lens equipped with the second diffractive structure of FIG. 3.

FIG. 6 shows the intensity distribution of a lens 1, onto which just a second diffractive structure 7 according to the middle diagram of FIG. 3 has been plotted (x-axis: distance D from the lens [mm]; y-axis: relative intensity I [1]). As shown, the positive order focal points $F_{2,1}$, $F_{2,2}$, etc. are assigned substantially the same intensity component as the negative order focal points $F_{2,-1}$, $F_{2,-2}$, etc.

As shown in FIG. 3, the grating periods $p_1(r)$ and $p_2(r)$ are of equal magnitude, such that, according to FIGS. 5 and 6, the first positive focal point $F_{1,1}$ of the first diffractive structure 6 is located at a distance from the refractive focal point $F_r$ which corresponds to the distance of the first positive focal point $F_{2,1}$ of the second diffractive structure 7.

According to the bottom diagram of FIG. 3, the assembled, "overlapped" diffractive structure 5 is obtained by additive overlapping of the two structures 6, 7 (x-axis: radius $r^2$ [mm$^2$]; y-axis: profile depth T [mm]). The overlapped diffractive structure 5 has a profile 14 with rising and falling flanks 15, 16, such that the profile 14 of the diffractive structure 5 rises monotonically substantially within one period. The diffractive structure 5 with the profile 14 is applied to one of the sides 2, 3 of the lens 1, see FIG. 4. To simplify production, the profiles 8, 11, 14 may have rounded or chamfered flanks 9, 10, 12, 13, 15, 16.

As is shown in the three diagrams of FIG. 3, the profile 8 of the first diffractive structure 6 rises monotonically within the period $p_1(r)$ and the profile 11 of the second diffractive structure 7 has a minimum in the first half of the period $p_2(r)$ and a maximum in the second half of the period. This results in the profile 14 of the overlapped diffractive structure 5 rising monotonically within the period $p_1(r)$, $p_2(r)$ and thus having just a maximum within this period. In one alternative embodiment (not shown), the second diffractive structure 7 could also have the maximum in the first half of the period $p_2(r)$ and the minimum in the second half of the period, which then leads to an overlapped diffractive structure 5 with two maxima per period. For manufacturing reasons, the former variant with just one maximum per period is preferable.

Figure 7:
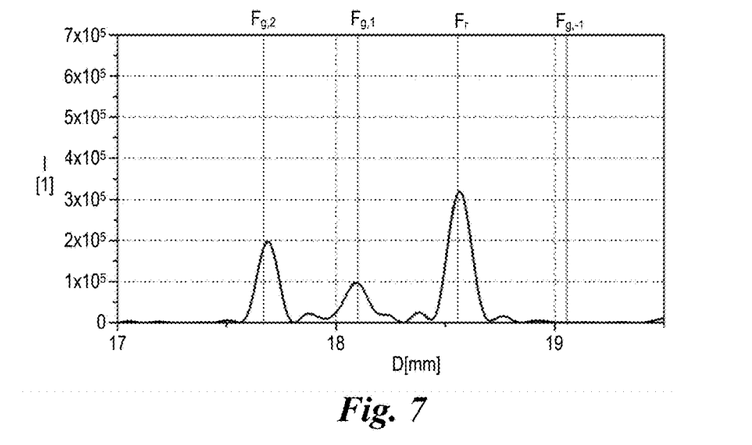
FIG. 7 shows the intensity distribution of the lens according to the invention of FIG. 1.

FIG. 7 shows the intensity distribution of the lens 1 into which the diffractive structure 5 consisting of the added or overlapped structures 6, 7 has been incorporated (x-axis: distance D from the lens [mm]; y-axis: relative intensity I [1]). The refractive focal point $F_r$ is here used for distance vision, the first positive diffractive focal point $F_{g,1}$ corresponds in its position to the first (positive) order focal points $F_{1,1}$, $F_{2,1}$ of the diffractive structures 6, 7 and is used for intermediate vision, and the second positive diffractive focal point $F_{g,2}$ corresponds in its position to the second (positive) order focal points $F_{1,2}$, $F_{2,2}$ of the diffractive structures 6, 7 and is used for near vision. Alternatively, the gradients of the flanks 9, 10, 12, 13 could each be reversed, whereby then for example the refractive focal point $F_r$ could be used for near vision and the first order $F_{1,1}$, $F_{2,1}$ or second order $F_{1,2}$, $F_{2,2}$ diffractive focal points for intermediate or distance vision.

The two structures 6, 7 may in each case be applied either to the entire surface of the side 2, 3 of the lens 1 or merely zonally, as shown in FIG. 1. Thus, for example, the combined structure 5 may be applied merely in the innermost zone $Z_1$, i.e. in the central region, of the lens 1. In a surrounding annular zone $Z_2$ just one of the two structures 6, 7 may be applied, and in an outermost annular zone $Z_3$ none of the structures 5, 6, 7. This results in an intensity distribution dependent on pupil size, wherein the weighting of the intensity at the refractive focal point $F_r$ increases as pupil size increases.

Alternatively or in addition, this effect may be achieved by apodising the structures 5, 6, 7. This means that the depth T of the profiles 8, 11, 14 of the structures 5, 6, 7 decreases as lens radius r increases (not shown in FIG. 3).

Figure 8:
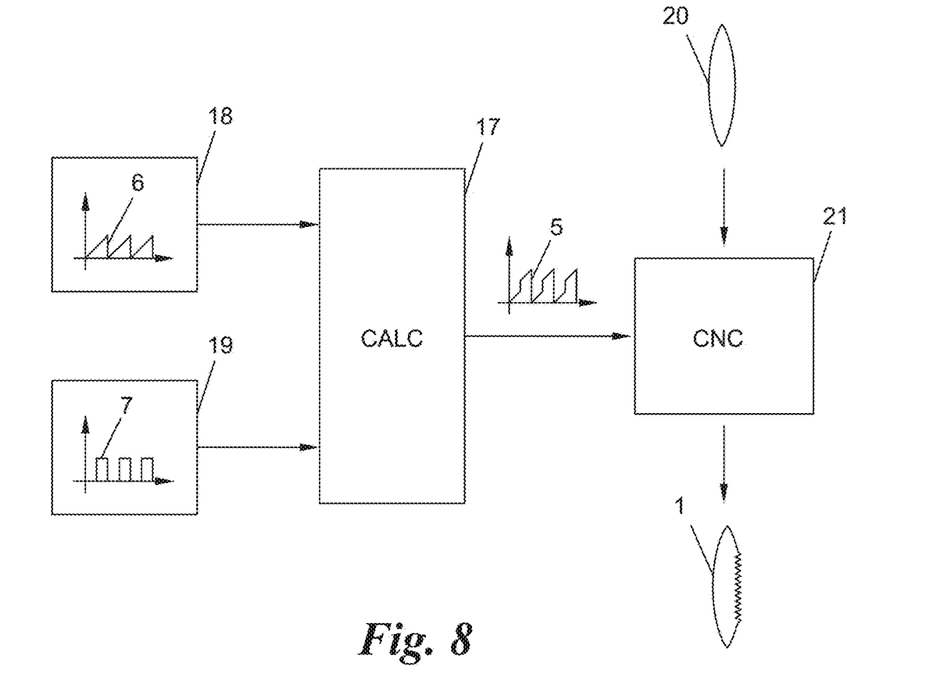
FIG. 8 shows a schematic block diagram of a first embodiment of the method according to the invention for producing the lens of FIG. 1.
Figure 9:
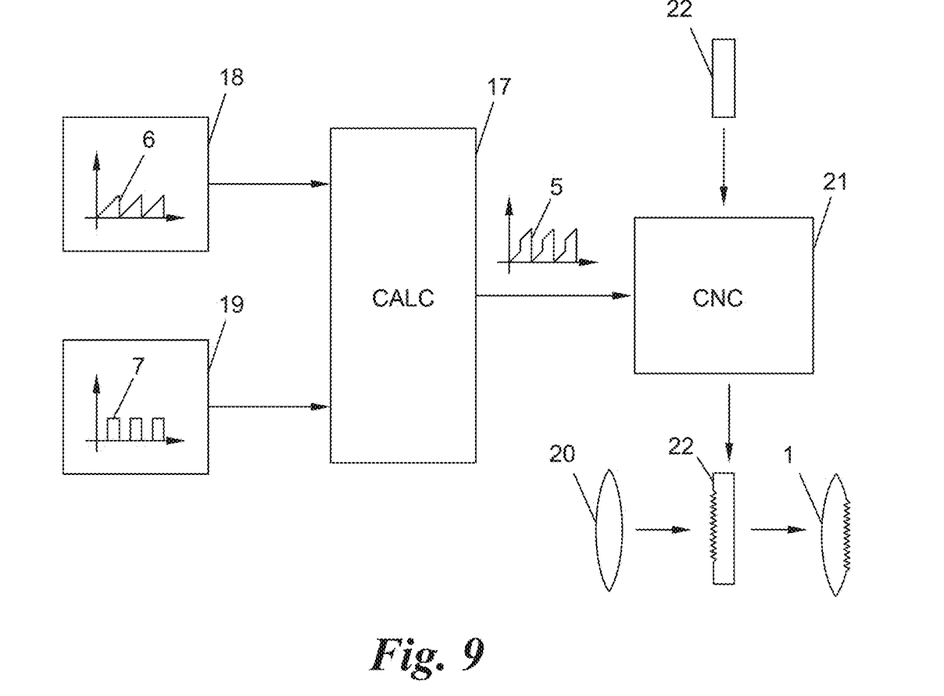
FIG. 9 shows a schematic block diagram of a second embodiment of the method according to the invention for producing the lens of FIG. 1.

FIGS. 8 and 9 show two variants of the method for producing the multifocal lens 1. To calculate the diffractive structure 5, also known as an "overlapping structure" 5, the first diffractive structure 6, which has an intensity distribution which is asymmetric around the refractive focal point $F_r$, and the second diffractive structure 7, which has an intensity distribution which is substantially symmetric around the refractive focal point $F_r$, is overlapped, for example added, in a computing unit 17. The structures 6, 7 may be made available to the computing unit 17 by means of storage devices 18, 19 or in the computing unit 17 itself.

FIG. 8 shows a first variant of the production process, in which the overlapping structure 5 calculated in the computing unit 17 is incorporated into a lens blank 20, for example by machining such as turning on a lathe 21, in order in this way to produce the multifocal lens 1. In this way, for example, the lens blank 20 is turned about its optical axis and the turning tool of the lathe 21 incorporates the overlapping structure 5 into the lens blank 20 during turning of the lens blank 20. After machining, the lens 1 may optionally be polished.

The lens blank 20 could however also merely be a processable starting material for a 3D printer, with incorporation of the overlapping structure 5 into the lens blank 5 then proceeding by 3D printing of the starting material 20 to yield the multifocal lens 1.

FIG. 9 shows a second variant of the production process, in which the overlapping structure 5 calculated in the computing unit is initially incorporated as a negative into a moulded blank 22, for example again by means of a lathe 21 or a 3D printer. Then, a lens material 20 is brought into contact with the moulded blank 22 in order in this way to produce the multifocal lens 1. The lens material 20 may for example already have been prefabricated into a lens blank, into which the overlapping structure 5 is pressed or impressed by means of the moulded blank 22 acting as a "punch". Alternatively, the lens material 20 may be present in a liquid or viscous state and be cast onto the moulded blank, for example in a mould. The lens material 20 is then hardened, for example by the input of light or heat.

Figure 10:
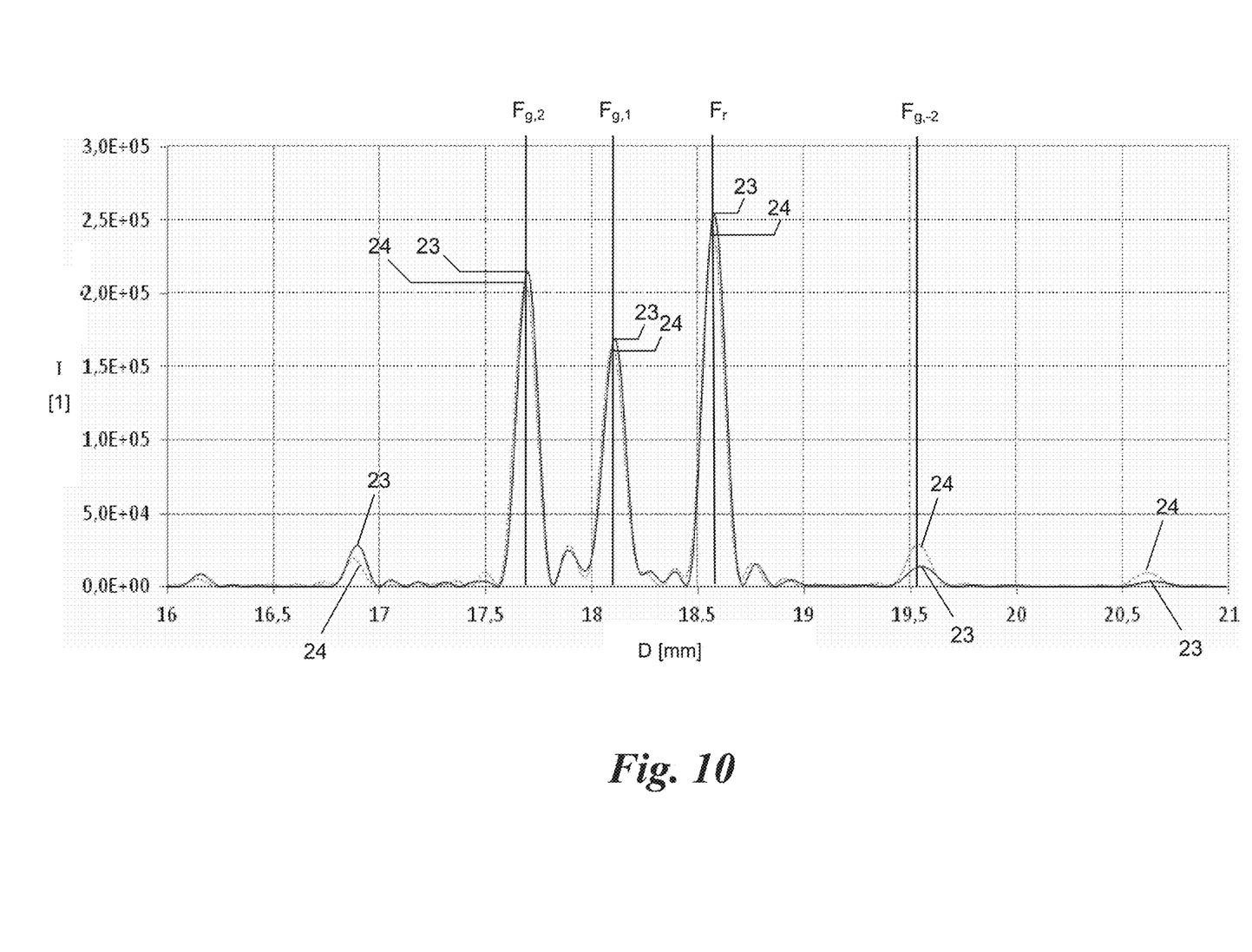
FIG. 10 shows a comparison of the intensity distribution of the lens according to the invention with a lens according to the prior art.

FIG. 10 shows a comparison of the intensity curve 23 of the lens 1 presented here with the intensity curve 24 of a lens according to the prior art (x-axis: distance D of the lens [mm]; y-axis: relative intensity I [1]). The comparative lens according to the prior art is provided with a structure in which two diffractive structures with asymmetric intensity distributions (for example saw-tooth-shaped structures) are overlapped, wherein the first order focal point of the first diffractive structure coincides with the second order focal point of the second diffractive structure.

This results in a similar intensity distribution curve in the region of the refractive focal point $F_r$. It is, however, very apparent from FIG. 10 that the lens 1 according to the prior art comprises greater intensity values in the region of the second negative focal point $F_{g,-2}$ of the combined diffractive structure 5 (or of the first negative focal point $F_{2,-1}$ of the second diffractive structure 7). In contrast, in the case of the lens 1 presented here, non-usable, negative order intensities are shifted into usable positive orders, as is apparent from the markedly increased intensities of the curve 17 at the focal points $F_{g,1}$ and $F_{g,2}$ and the markedly reduced intensity of the curve 23 at the focal point $F_{g,-2}$. A more intensely coloured and higher contrast image is thus obtained for the user of the described lens 1 than with lenses according to the prior art.

The invention is accordingly not limited to the embodiments shown but rather comprises all variants, modifications and combinations thereof which fall within the scope of the appended claims.

The invention claimed is:

1. A multifocal intraocular or contact lens, having a refractive focal point ($F_r$) and a first and a second diffractive structure, which at least partially overlap,
   wherein the two diffractive structures are different,
   wherein a first order diffractive focal point ($F_{1,1}$) of the first diffractive structure coincides with a first order diffractive focal point ($F_{2,1}$) of the second diffractive structure.

2. The multifocal intraocular or contact lens according to claim 1, wherein the two diffractive structures have different intensity distributions.

3. The multifocal intraocular or contact lens according to claim 1, wherein the first diffractive structure has an intensity distribution that is asymmetric around the refractive focal point (Fr) and the second diffractive structure has an intensity distribution that is symmetric around the refractive focal point (Fr).

4. The multifocal intraocular or contact lens according to claim 1, wherein the profiles of the two diffractive structures have the same period length ($p_1$, $p_2$), wherein the profile of the first diffractive structure is monotonically rising within the period ($p_1$) and the profile of the second diffractive structure has a minimum in the first half of the period ($p_2$) and a maximum in the second half of the period.

5. The multifocal intraocular or contact lens according to claim 1, wherein the first diffractive structure has a profile with saw-tooth, echelette or kinoform shape.

6. The multifocal intraocular or contact lens according to claim 1, wherein the second diffractive structure has a profile with rectangular, trapezoidal or sinusoidal shape.

7. The multifocal intraocular or contact lens according to claim 1, wherein at least one of the profiles has rounded-off or bevelled flanks.

8. The multifocal lens according to claim 1, wherein the two diffractive structures are apodized.

9. A method for producing the multifocal intraocular or contact lens according to claim 1, comprising the steps of:
   a) providing a lens blank with a refractive focal point (Fr);
   b) calculating an overlapping structure from the first diffractive structure and the second diffractive structure;
   c) incorporating the overlapping structure into the lens blank to produce the multifocal lens.

10. The method according to claim 9, wherein the incorporation of the overlapping structure into the lens blank is realised by turning.

11. A method for producing the multifocal intraocular or contact lens according to claim 1, comprising the steps of:
   a) providing a moulded blank;
   b) calculating an overlapping structure from the first diffractive structure and the second diffractive structure;
   c) incorporating the overlapping structure as a negative into the moulded blank; and d) producing the multifocal lens by bringing a lens material into contact with the moulded blank, wherein a refractive focal point ($F_r$) is also given to the lens material.

12. The method according to claim 11, wherein the bringing into contact is realised by casting the lens material onto the moulded blank and hardening of the lens material.

13. The method according to claim 9, wherein the first diffractive structure has an intensity distribution that is asymmetric around the refractive focal point (Fr) and the second diffractive structure has an intensity distribution that is symmetric around the refractive focal point (Fr).

14. The method according to claim 9, wherein the profiles of the two diffractive structures have the same period length (p1, p2), wherein the profile of the first diffractive structure is monotonically rising within the period (p1) and the profile of the second diffractive structure has a minimum in the first half of the period (p2) and a maximum in the second half of the period (p2).

15. The method according to claim 9, wherein at least one of the two diffractive structures has rounded-off or bevelled flanks.

16. The method according to claim 9, wherein the two diffractive structures are apodized.

17. The method according to claim 11, wherein the first diffractive structure has an intensity distribution that is asymmetric around the refractive focal point (Fr) and the second diffractive structure has an intensity distribution that is symmetric around the refractive focal point (Fr).

18. The method according to claim 11, wherein the profiles of the two diffractive structures have the same period length (p1, p2), wherein the profile of the first diffractive structure is monotonically rising within the period (p1) and the profile of the second diffractive structure has a minimum in the first half of the period (p2) and a maximum in the second half of the period (p2).

19. The method according to claim 11, wherein at least one of the two diffractive structures has rounded-off or bevelled flanks.

20. The method according to claim 11, wherein the two diffractive structures are apodized.

* * * * *

UNITED STATES PATENT AND TRADEMARK OFFICE
CERTIFICATE OF CORRECTION

| | | |
|---|---|---|
| PATENT NO. | : 10,524,899 B2 | Page 1 of 1 |
| APPLICATION NO. | : 15/765385 | |
| DATED | : January 7, 2020 | |
| INVENTOR(S) | : Lux et al. | |

It is certified that error appears in the above-identified patent and that said Letters Patent is hereby corrected as shown below:

On the Title Page

Item (73), the Assignee should read:
--(73) Assignee: Rayner Intraocular Lenses Limited, West Sussex (GB)--

Signed and Sealed this
Nineteenth Day of May, 2020

Andrei Iancu
*Director of the United States Patent and Trademark Office*